United States Patent
Köhler et al.

(10) Patent No.: US 12,036,156 B2
(45) Date of Patent: Jul. 16, 2024

(54) SURGICAL TABLE AND METHOD FOR CONTROLLING A SURGICAL TABLE

(71) Applicant: TRUMPF MEDIZIN SYSTEME GMBH + CO. KG, Saalfeld (DE)

(72) Inventors: Matthias Köhler, Saalfeld (DE); Matthias Jäger, Rudolstadt (DE)

(73) Assignee: Baxter Medical Systems GmbH + Co. KG, Saalfeld (DE)

( * ) Notice: Subject to any disclaimer, the term of this patent is extended or adjusted under 35 U.S.C. 154(b) by 0 days.

(21) Appl. No.: 17/529,838

(22) Filed: Nov. 18, 2021

(65) Prior Publication Data
US 2022/0151854 A1 May 19, 2022

(30) Foreign Application Priority Data

Nov. 19, 2020 (EP) .................................... 20208606

(51) Int. Cl.
*A61G 13/08* (2006.01)
*A61G 13/02* (2006.01)
*A61G 13/04* (2006.01)

(52) U.S. Cl.
CPC ............. *A61G 13/08* (2013.01); *A61G 13/02* (2013.01); *A61G 13/04* (2013.01)

(58) Field of Classification Search
CPC ........ A61G 13/02; A61G 13/04; A61G 13/08; A61G 13/10; A61G 2203/10;
(Continued)

(56) References Cited

U.S. PATENT DOCUMENTS

| | | | |
|---|---|---|---|
| 7,089,612 B2 * | 8/2006 | Rocher | A61G 13/08 5/616 |
| 2003/0195644 A1 * | 10/2003 | Borders | A61G 12/00 340/568.1 |

(Continued)

FOREIGN PATENT DOCUMENTS

| | | |
|---|---|---|
| CN | 111297615 A | 6/2020 |
| EP | 2702974 A2 | 3/2014 |

(Continued)

OTHER PUBLICATIONS

European Search Report in related application EP20208606, dated May 3, 2021, 8 pages.

(Continued)

*Primary Examiner* — David R Hare
(74) *Attorney, Agent, or Firm* — Barnes & Thornburg LLP

(57) ABSTRACT

A surgical table comprises a base, components, and a controller. The controller is configured to store a geometric collision model including object model datasets of the components, of the base, and of a supporting surface and motion compute datasets of the base and of the components. The controller is configured to execute an anti-collision algorithm defining ranges of motion of the base and of the components based on a specific geometric collision model, and to control a drive to move the base and the components within the defined ranges of motion such that a collision is prevented. The controller is configured to store a defined initial geometric collision model of a configuration and to adapt the initial geometric collision model to an actual geometric collision model according to an actual configuration.

20 Claims, 2 Drawing Sheets

(58) Field of Classification Search
CPC .......... A61G 2203/72; A61G 2203/726; G06T 7/70; G06T 2210/12; G06T 2210/21; G16H 20/40; G16H 40/63
USPC .............................................. 5/610; 345/958
See application file for complete search history.

(56) References Cited

U.S. PATENT DOCUMENTS

| | | | |
|---|---|---|---|
| 2003/0230724 A1 | 12/2003 | Koops et al. | |
| 2006/0080777 A1 | 4/2006 | Rocher et al. | |
| 2018/0296418 A1 | 10/2018 | Graf et al. | |
| 2019/0142667 A1* | 5/2019 | Paul | A61G 7/012 5/600 |
| 2020/0188206 A1* | 6/2020 | Hempel | G16H 40/63 |

FOREIGN PATENT DOCUMENTS

| | | | |
|---|---|---|---|
| EP | 3667675 A1 | 6/2020 |
| WO | 2015120008 A1 | 8/2015 |
| WO | 2016069663 A1 | 5/2016 |

OTHER PUBLICATIONS

European Search Report in related application EP21209402, dated Dec. 20, 2021, 8 pages.
Chinese Office Action issued by the Chinese Patent Office on Nov. 13, 2023, in Chinese Patent Application No. 2021114004686, and its English translation (12 pages).

* cited by examiner

SURGICAL TABLE AND METHOD FOR CONTROLLING A SURGICAL TABLE

CROSS-REFERENCE TO RELATED APPLICATIONS

This application claims the benefit of European Patent Application Serial No. 20208606.2, filed Nov. 19, 2020, the entire disclosure of which is incorporated herein by reference in its entirety.

BACKGROUND

Surgical tables provided with a collision prevention function are known. For example, EP 3 667 675 A1 discloses a medical apparatus, particularly a surgical table, provided with such a collision prevention function. Due to this function, a collision between components of the surgical table and other components and a floor are prevented. For this function, a configuration of the surgical table is reproduced by means of virtual bounding boxes and, furthermore, the current positions and orientations of the bounding boxes are used to determine an imminent collision of the real components of the surgical table.

However, this collision prevention function is based on standard geometric collision models representing a basic configuration of the surgical table. Therefore, if an actual configuration of the surgical table does not correspond to the standard geometric collision model, there may be either a risk of collision or ranges of movement are limited such that required postures of the components cannot be reached.

Therefore, the object underlying the disclosure is to eliminate the above-mentioned disadvantages and to provide a surgical table which enables a safe use independent from its configuration.

SUMMARY

The present disclosure includes one or more of the features recited in the appended claims and/or the following features which, alone or in any combination, may comprise patentable subject matter.

According to an aspect of the present disclosure, a surgical table is provided. The surgical table comprises a base configured to be supported by a supporting surface, the base provided with a base drive configured to move at least a portion of the base relative to the supporting surface; a plurality of components supportable by the base, one or more of the plurality of components being provided with a respective component drive configured to move the respective component with respect to another one of the plurality of components or to the base. The base and at least a subset of the plurality of components when supported by the base form a configuration of the surgical table. The surgical table further comprises a controller configured to store, and adapt, a geometric collision model including: object model datasets defining a respective geometry of each of the plurality of components, of the base, and of the supporting surface; and motion compute datasets defining kinematic relationships and ranges of motion of the base, and of the plurality of components. The controller is configured to store as the geometric collision model a pre-defined initial geometric collision model of a baseline configuration of the surgical table and to adapt the initial geometric collision model to an actual geometric collision model according to an actual configuration of the surgical table, and store said actual geometric collision model as the geometric collision model.

The controller is further configured to execute an anti-collision algorithm, defining respective ranges of motion of the base and each of the subset of the plurality of components supported by the base in dependence on the stored geometric collision model, the anti-collision algorithm being configured to control the base drive to move the at least a portion of the base, and to control the respective component drive to move the respective one of the plurality of components, only within the defined respective ranges of motion such that a collision between any of the subset of the plurality of components, the base, and the supporting surface is prevented.

The object model datasets are, e.g., bounding boxes, wherein a bounding box is an object-oriented virtual bounding box representing a cuboid box including one or several of the components or of the base. The motion compute datasets define kinematic relationships, i.e., motion vectors of the components and the base, and ranges of motion of the components with respect to one of the other components and to the base. Moreover, the geometric collision model comprises an arrangement of the several components with respect to one another and to the base, and a respective posture of the base and of the several components.

The anti-collision algorithm defines, under consideration of the object model datasets and the motion compute datasets, respective ranges of motions of the base and of the several components driven by the respective drive. In particular, the anti-collision algorithm calculates whether an intersection point of at least two bounding boxes exists. If such an intersection point exists, a collision is assumed and the range of motion is accordingly reduced.

The controller stores an initial geometric collision model of a defined configuration which can be regarded as a basic configuration of the surgical table. This basic configuration may either be a configuration including a minimum configuration, i.e., for example merely the base and a back plate of the tabletop, or a configuration suitable for a wide field of surgical interventions.

Furthermore, the controller adapts the initial geometric collision model according to an actual configuration.

The adaption of the initial geometric collision model to the actual configuration considers, for example, an exchange of one or several of the components, a modification of a posture of one of the components driven or not driven by the respective drive, or a removal of one of the components. Due to the adaption to the actual configuration, a risk of collision can be avoided or ranges of movement can be enlarged such that a required posture of the components can be reached although they are located outside the ranges of motions based on the initial geometric collision model.

The base may comprise a column and a column head. The column head may be movable relative to the column, and as such may be the at least a portion of the base that is movable relative to the support surface by the base drive. Alternatively, the column head may be integrated into the column, and the entire base is movable relative to the support surface by the base drive, e.g. by pivoting relative to the support surface. The base may further comprise a chassis.

It is noted that moving at least a portion of the base relative to the support surface does not refer to movement along the support surface; the surgical table is fixed on, or to, the support surface, whether by brakes on wheels of the base, or by separate fixings. Movement relative to the support surface refers to pivoting, rolling, or movement away from and towards the support surface.

The respective component drive of the one or more of the plurality of components provided with such a drive is configured to move the respective component either relative (e.g. by pivoting, tiling, or moving up or down) to an adjacent one of the plurality of components, or, if the component is supported directly by the base, for example if it is adjacent a portion of the base, such as the column head, the component drive is configured to move the component relative to the base.

The base drives and component drives are controlled so that a collision between any of the plurality of components, the base, and the supporting surface is prevented. As such, if a component is moved by a respective component drive, it is prevented from colliding with any of the other components, the base, or the supporting surface. As movement of one of the components may also move other components attached to said components, the anti-collision algorithm also prevents a collision of any attached components with the remaining components, the base, or the supporting surface.

Similarly, as at least a portion of the base is moved by the base drive, not only is the base prevented from colliding with the support surface, the plurality of components, and itself, but the components supported by the base which move when the at least a portion of the base moves are prevented from colliding with other components, the support surface, or the base.

According to another embodiment of the surgical table, a plurality of configurations of the surgical table, each having a different arrangement of the subset of the plurality of components or a different subset of the plurality of components, are pre-defined, and the controller is further configured to store an initial geometric collision model for each of the pre-defined plurality of configurations.

If a plurality of different configurations are defined and the initial geometric collision models thereof are stored, and an actual configuration can be closer to one of the defined configurations so that the efforts for adapting the initial geometric collision model to the actual geometric collision model are less.

According to another embodiment of the surgical table, the surgical table comprises a sensor configured to detect an attachment of one of the plurality of components to a specific location of the surgical table, and the controller is configured to select one of the plurality of initial geometric collision models as the geometric collision model according to a detection of the attachment of the one of the components to the specific location of the surgical table.

By this feature, the geometric collision model can be selected automatically in case that, for example, an additional component is attached to one of the present components at an end of the tabletop. Therefore, the initial geometric collision model considering this specific component at this location is selected so that, e.g., the range of motion of the present component or of the entire tabletop is reduced due to a larger length of the tabletop because of the additional component which would collide with the floor in case of a tilting around the axis perpendicular to the longitudinal axis of the tabletop in a range of motion of the initial geometric collision model.

According to another embodiment of the surgical table, the surgical table comprises a user interface, and the controller is configured to adapt the initial geometric collision model to the actual geometric collision model in response to an input to the user interface.

By the adaption of the initial geometric collision model due to the input to the user interface, for example, an initiation of a detection of further component by a sensor or input of an attached additional component can be performed easily.

According to another embodiment of the surgical table, the input to the user interface is a continuous instruction to move at least one of the subset of the plurality of components, and/or the base, to an intended position beyond its respective range of motion defined by the anti-collision algorithm, and the controller is configured to apply the intended position as a limit of a modified range of motion and to adapt the stored geometric collision model to the actual geometric collision model based on the limit of the modified range of motion of the actual configuration.

In this embodiment, it is possible to move at least one of the components, e.g., by continuously pressing a button, beyond its range of motion defined based on the initial geometric collision model. This can be done if, in the actual configuration, e.g., a component having a smaller dimension in the longitudinal direction of the tabletop is used so that the range of motion for tilting around the axis perpendicular to the longitudinal direction is actually larger than defined based on the initial geometric collision model. In this case, an operator is responsible for a safe operation and for preventing the collision.

According to an another embodiment of the surgical table, the controller is configured to control a motion of the at least one of the subset of the plurality of components, and/or the base, beyond its respective range of motion defined by the anti-collision algorithm at a velocity reduced with respect to a velocity for moving the at least one of the subset of the plurality of components within its respective range of motion defined by the anti-collision algorithm.

By this feature, a risk for a collision is reduced since the operator can more easily follow up the motion of the component.

According to another embodiment of the surgical table, the controller is configured to signal a, or the, motion of the at least one of the subset of the plurality of components, and/or the base, beyond its respective range of motion defined in the anti-collision algorithm.

The signaling of the motion beyond the respective range of motion of the one of the components enhances safety since the controller points out the motion in a dangerous region.

According to another embodiment, the surgical table comprises a, or the, sensor configured to detect an attachment of one of the plurality of components to a specific location of the surgical table, and the controller is configured to adapt the stored geometric collision model to the actual geometric collision model based on a detection of the one of the plurality of components attached to the specific location of the surgical table.

By these features, the initial geometric collision model can be adapted automatically to a suitable actual configuration.

According to another embodiment, the surgical table comprises a collision sensor configured to detect a collision, or an imminent collision, between one of the plurality of components and another one of the subset of the plurality of components, the base, the supporting surface, or an obstacle, and the controller is configured to adapt the stored geometric collision model such that the anti-collision algorithm defines the respective ranges of motion of the base and of the subset of the plurality of components such that the collision is prevented.

In this embodiment, the initial geometric collision model can be adapted additionally to circumstances which not directly relate to a configuration of the surgical table. Instead, additional, as the case may be, temporary obstacles in the region of the surgical table can be recognized and the geometric collision model can be adapted such that a subsequence collision with the obstacle is prevented.

Optionally, the object model datasets comprise bounding boxes, and the anti-collision algorithm calculates whether an intersection point of at least two bounding boxes exists.

According to another aspect of the present disclosure, a method for controlling a surgical table includes the step: initiating a motion of at least one of the subset of the plurality of components, and/or the at least a portion of the base, to reach an intended position of the at least one of the subset of the plurality of components, and/or the base, by controlling the respective component drive, and/or the base drive, by the controller; manually checking whether the intended position is reached; if the intended position of the at least one of the subset of the plurality of components, and/or the base, cannot be reached within the ranges of motion defined by the anti-collision algorithm, then manually continuously providing input to the controller, to control the respective component drive, and/or the base drive, such that the intended position of the at least one of the subset of the plurality the components, and/or the base, beyond the ranges of motion defined by the anti-collision algorithm, is reached; adapting the stored geometric collision model according to modified ranges of motion necessary for reaching the intended position, wherein the stored geometric collision model is adapted by applying the positions of the subset of the plurality of components and the base necessary for reaching the intended position of the at least one of the subset of the plurality of components, and/or the base, as limits of the ranges of motion; storing the adapted geometric collision model; and subsequently defining the respective ranges of motion by the anti-collision algorithm based on the stored geometric collision model and controlling the base drive and the respective component drive to move within the ranges of motion defined based on the stored geometric collision model.

Due to this method, the ranges of movement can be enlarged such that a required posture of the components can be reached although they are located beyond the ranges of motion based on the initial geometric collision model. Thus, the operation of the surgical table and, therefore, the provision of suitable postures for a surgical the intervention is facilitated.

In another embodiment of the method, the method includes the step: controlling a motion of the at least one of the subset of the plurality of components, and/or the base, beyond their respective ranges of motion defined by the anti-collision algorithm at a velocity reduced with respect to a velocity for moving the at least one of the subset of the plurality of components, and/or the base, within the respective range of motion defined by the anti-collision algorithm.

By this feature, a risk for a collision is reduced since the operator can more easily follow up the motion of the component.

In another embodiment of the method, it includes the step: signaling a, or the motion, of the at least one of the plurality of components and/or the base, beyond the respective range of motion defined by the anti-collision algorithm.

Due to this embodiment, the operator is warned that the surgical table is in a state outside the allowed ranges of motion so that an improved possibility for recognizing a potential risk for a collision is enabled.

In another embodiment of the method, it includes the step: resetting the stored geometric collision model to the initial geometric collision model when subsequently waking up the controller from a standby.

By this step, the original grade of safety is restored so that a safe use of the surgical table is possible.

In another embodiment of a method, it includes the step: when detecting a collision, or an imminent collision, within the range of motion defined based on the stored geometric collision model, adapting the stored geometric collision model such that the collision is prevented.

By this method step, the initial geometric collision model can be adapted additionally to circumstances which not directly relate to a configuration of the surgical table. Instead, additionally, as the case may be, temporary obstacles in the region of the surgical table can be recognized and the geometric collision model can be adapted such that a subsequence collision with the obstacles is prevented.

The term "stored" geometric collision model may refer to an (active) initial geometric collision model, or, if the initial geometric collision model has been adapted, the adapted, or actual, geometric collision model.

According to another aspect of the present disclosure, a method for controlling a surgical table includes the step: initiating a motion of at least one of a subset of a plurality of components, and/or at least a portion of a base, to reach an intended position of the at least one of the subset of the plurality of components, and/or the base, by controlling a respective component drive, and/or a base drive, by a controller; manually checking whether the intended position is reached; if the intended position of the at least one of the subset of the plurality of components, and/or the base, cannot be reached within ranges of motion defined by a anti-collision algorithm, then manually continuously providing input to the controller, to control the respective component drive, and/or the base drive, such that the intended position of the at least one of the subset of the plurality the components, and/or the base, beyond the ranges of motion defined by the anti-collision algorithm, is reached; adapting a stored geometric collision model according to modified ranges of motion necessary for reaching the intended position, wherein the stored geometric collision model is adapted by applying positions of the subset of the plurality of components and the base necessary for reaching the intended position of the at least one of the subset of the plurality of components, and/or the base, as limits of the ranges of motion; storing the adapted geometric collision model; and subsequently defining the respective ranges of motion by the anti-collision algorithm based on the stored geometric collision model and controlling the base drive and the respective component drive to move within the ranges of motion defined based on the stored geometric collision model.

Additional features, which alone or in combination with any other feature(s), such as those listed above and/or those listed in the claims, can comprise patentable subject matter and will become apparent to those skilled in the art upon consideration of the following detailed description of various embodiments exemplifying the best mode of carrying out the embodiments as presently perceived.

BRIEF DESCRIPTION OF THE DRAWINGS

The detailed description particularly refers to the accompanying figures in which.

DETAILED DESCRIPTION

Figure 1:
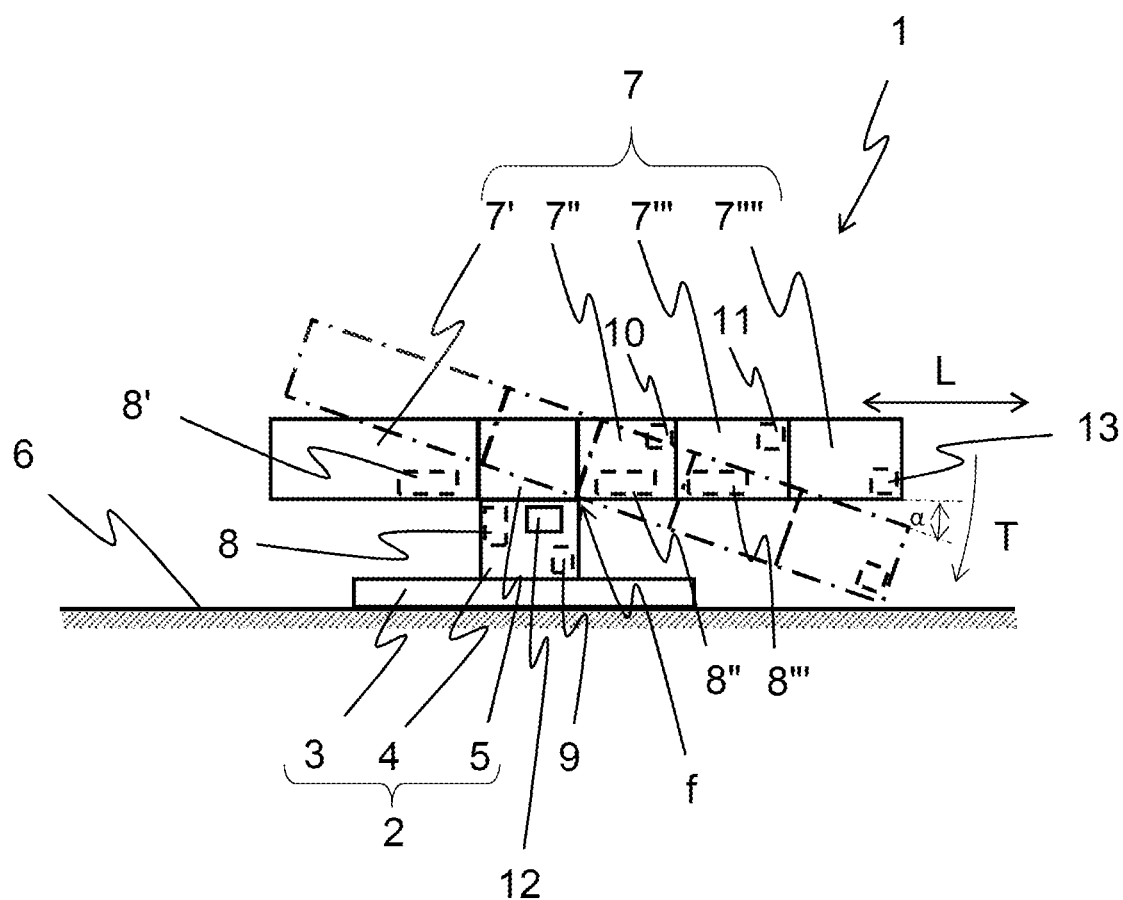
FIG. 1 shows a principle illustration of a first configuration of a surgical table.

FIG. 1 shows a principle illustration of a first configuration of a surgical table 1. The surgical table 1 comprises a base 2. The base 2 comprises a chassis 3, a column 4 and a column head 5. The base 2 is supported by a floor as being a supporting surface 6. In an alternative embodiment, the base 2 does not comprise the chassis 3 but the column 4 is fixedly attached to the supporting surface 6. In a further alternative embodiment, the base 2 comprises the column head 5 integrated into the column 4.

Further, the surgical table 1 comprises several components 7 movable with respect to one another and to the base 2. In particular, the surgical table 1 comprises a leg section 7', a back plate 7", an upper back plate 7''', and a head plate 7'''' as being the several components 7. The several components 7 form a tabletop of the surgical table 1. The tabletop has a longitudinal direction L.

Some of the several components 7, in this embodiment, the leg section 7', the back plate 7", and the upper back plate 7''' are provided with a drive 8', 8", 8''' for moving a respective component with respect to another component and to the base 2. In alternative embodiments, other ones of the components 7 or all of the components are provided with respective drives.

The leg section 7' is movable with respect to the base 2 around an axis perpendicular to the longitudinal direction L. The leg section 7' is moved by a drive 8' for moving the leg section 7' around the axis perpendicular to the longitudinal direction L.

The back plate 7" is movable with respect to the base 2 around an axis perpendicular to the longitudinal direction L. The back plate 7" is moved by a drive 8" for moving the back plate 7" around the axis perpendicular to the longitudinal direction L.

The upper back plate 7''' is movable with respect to the base 2 around an axis perpendicular to the longitudinal direction L. The upper back plate 7''' is moved by a drive 8''' for moving the upper back plate 7''' around the axis perpendicular to the longitudinal direction L.

The head plate 7'''' is movable with respect to the base 2 around an axis perpendicular to the longitudinal direction L. The head plate 7'''' is to be moved manually and it is provided with a clamping mechanism for being fixed in an intended posture by a manual intervention. For changing a posture of the head plate 7'''', the clamping mechanism is released and clamped again when the head plate 7'''' has been moved into the intended posture.

Additionally to the feature that the leg section 7', the back plate 7", the upper back plate 7''', and the head plate 7'''' are respectively movable with respect to the base 2 around a respective axis perpendicular to the longitudinal direction L, the leg section 7', the back plate 7", the upper back plate 7''', and the head plate 7'''' are respectively movable with respect to one another around the respective axis perpendicular to the longitudinal direction L. Since the several components 7 are movable with respect to the base 2, the several components 7 are also movable with respect to the supporting surface 6.

The column 4 is formed as a height adjustable column and, therefore, the several components 7 forming the tabletop can be moved with respect to the supporting surface 6 by a motion of the base 2. For moving the several components 7 with respect to the supporting surface 6, the base 2 is provided with a drive 8, in particular, an electric drive. The several components 7 are movable with respect to the base 2 and to the supporting surface 6 in a height adjustable manner such that the distance between the tabletop and the supporting surface 6 is varied, around the axis perpendicular to the longitudinal direction L, and around an axis parallel to the longitudinal direction.

Figure 2:
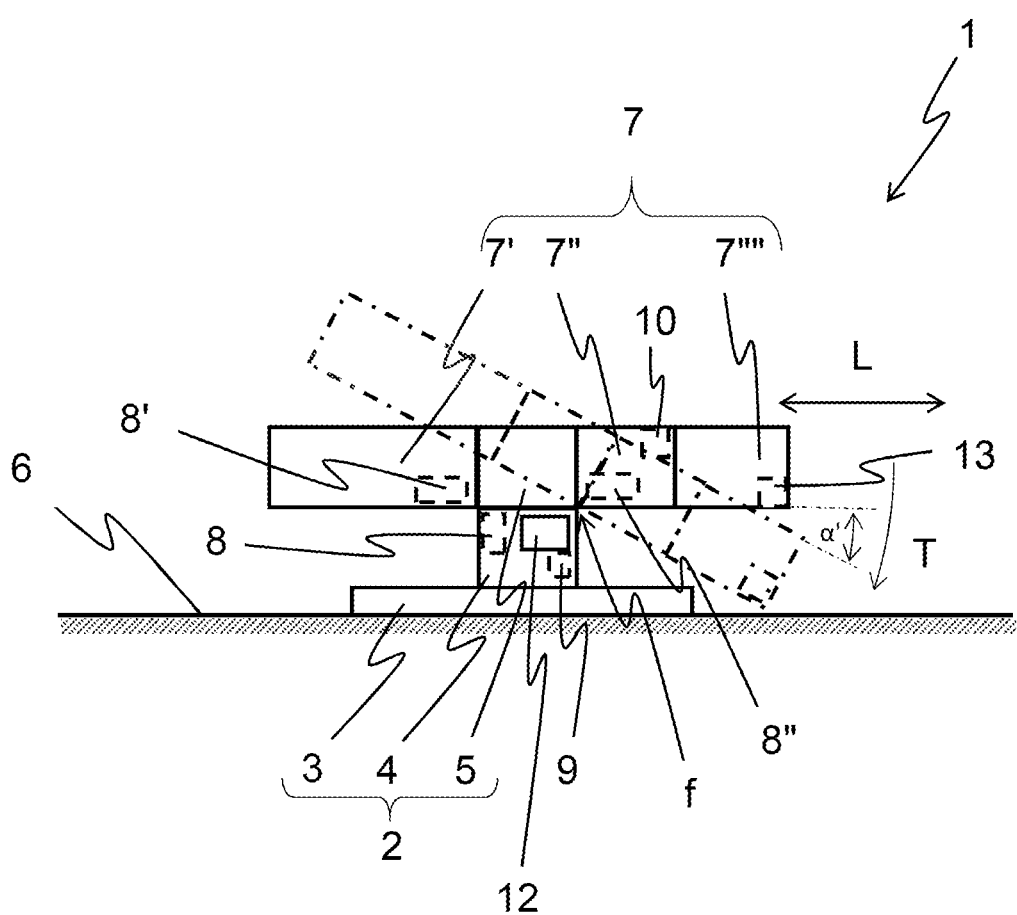
FIG. 2 shows a principle illustration of a second configuration of the surgical table.

FIG. 2 shows a principle illustration of a second configuration of the surgical table 1. The second embodiment distinguishes from the first configuration in that one of the several components 7, namely the upper back plate 7''', and a sensor 11 are not provided. The remaining features are identical.

The following description relates to FIG. 1 and FIG. 2. The base 2 and the several components 7 form a respective configuration of the surgical table 1. Different arrangements or provisions of different ones of the several components 7 form several different configurations.

The surgical table 1 comprises a controller 9. The controller 9 is configured to store a geometric collision model of the surgical table 1.

The geometric collision model includes object model datasets defining a respective geometry of the several components 7, of the base 2, and of the supporting surface 6 supporting the base 2. Furthermore, the geometric collision model includes motion compute datasets defining kinematic relationships and ranges of motion of the base 2 and of the several components 7. For defining the geometry, the model datasets include bounding boxes which are object oriented and which respectively correspond to the base 2 and to the several components 7. The bounding boxes respectively represent a virtual cuboid box including the base 2 or one of the several components 7. The bounding boxes are defined by the X, Y, and Z dimensions of the respective base 2 or at least one of the several components 7 and by a translation from the center of the bounding box to a rotation center in X, Y, Z direction The controller 9 is configured to execute an anti-collision algorithm defining respective ranges of motions of the base 2 and of the several components 7 driven by the respective drive 8, 8', 8" based on a specific geometric collision model. In particular, the anti-collision algorithm is executed such by the controller 9 that it defines the ranges of motion of the base 2 and of the components 7 based on the specific geometric collision model such that no collision between the components amongst themselves, with the base, and with the supporting surface occurs. For preventing the collision, the algorithm calculates whether an intersection point of at least two bounding boxes exists. If such an intersection point exists, a collision is assumed and the range of motion is accordingly reduced. Furthermore, the controller 9 controls the respective drives 8, 8', 8" to move the base 2 and the several components 7 within the defined ranges of motion such that a collision between the several components 7 amongst themselves, with the base 2, and with the supporting surface 6 are prevented.

The controller 9 is configured to store a beforehand defined initial geometric collision model of a beforehand defined configuration and to adapt the initial geometric collision model to an actual geometrical mission model according to an actual configuration.

The beforehand defined configuration represents a basic configuration of the surgical table 1. This basic configuration is a configuration according to FIG. 1. This configuration is suitable for a wide field of surgical interventions. Alternatively, several beforehand defined different configurations with different arrangements of the several components 7 are stored by the controller 9. One of these configurations may be a configuration according to the surgical table 1 of FIG. 2. A further one of these configurations may be a configuration including a minimum configuration, i.e., for example merely the base 2 and the back plate 7".

Furthermore, the surgical table 1 comprises a sensor 10 to detect an attachment of one of the components 7 to a specific location of the surgical table 1. In this embodiment, the sensor 10 detects the attachment of the upper back plate 7''', as to be seen in FIG. 1, or the head plate 7'''', as to be seen in FIG. 2, to the back plate 7". Moreover, the surgical table 1 comprises a further sensor 11 (FIG. 1) to detect an attachment of one of the components 7 to specific location of the surgical table 1. The further sensor 11 detects the attachment of one of the components 7, the head plate 7'''', to the upper back plate 7'''. Alternatively, only one sensor 10, 11 to detect an attachment of one of the components 7 to a specific location of the surgical table 1 is provided or more than two of these sensors 10, 11 are provided.

According to the detection of the attachment of one of the components 7 to a specific location of the surgical table 1, the controller 9 selects one of the initial geometric collision models. For example, referring to the shown embodiments, if the upper back plate 7''' attached to the back plate 7" as well as the head plate 7'''' attached to the upper back plate 7''' are detected by the sensors 10, 11, the controller 9 selects the configuration according to FIG. 1 and, therefore, executes the anti-collision algorithm based the initial geometric collision model of this configuration. If merely the head plate 7'''' attached to the back plate 7" is detected by the sensor 10, the controller 9 selects the configuration according to FIG. 2 and, therefore, executes the anti-collision algorithm based on the initial geometric collision model of this configuration. If several initial geometric collision models are possible due to the detected components, further information, such as a direction of a patient lying on the tabletop, is used as a decision criterion for selecting the initial geometric model.

In an alternative embodiment, the sensors 10, 11 are not used for selecting the geometric collision model but for modifying the used geometric collision model. Also in this alternative embodiment, the sensors 10, 11 detect the attachment of one of the several components 7 to a specific location of the surgical table 1.

In FIG. 1 and FIG. 2, by dash-and-dot lines, a respective posture of the tabletop including the several components 7 tilted about a pivot angle $\alpha$, $\alpha'$ in a direction T around a fulcrum f right before a collision of the head plate 7'''' occurs and the supporting surface 6 is shown. As to be seen from the figures, a maximum pivot angle $\alpha'$ in FIG. 2 is larger than the maximum pivot angle $\alpha$ in FIG. 1 and, therefore, the range of motion of the tilting around the fulcrum f of the tabletop in FIG. 2 can be larger than of the tilting around the fulcrum f of the tabletop in FIG. 1.

However, if, for example, the geometric collision model of the configuration of the surgical table 1 shown in FIG. 2, is used as the initial geometric collision model of the surgical table 1 in FIG. 1, there is the problem that the head plate 7'''' potentially collides with the supporting surface 6 since the maximum pivot angle $\alpha'$ allowed for the second embodiment is larger than the maximum pivot angle $\alpha$ suitable for the first embodiment.

Therefore, in this alternative embodiment, the controller 9 adapts the initial geometric collision model, namely the geometric collision model of the configuration of the surgical table 1 of FIG. 2, according to the detection of the attachment of the upper back plate 7''' between the back plate 7" and the head plate 7'''' by the sensors 10, 11 such that the smaller maximum pivot angle $\alpha$ is used. The initial geometric collision model is adapted to the actual geometric collision model by considering the object model dataset and the motion compute dataset of the upper back plate 7''' between the back plate 7" and the head plate 7''''. In particular, for adapting the initial geometric collision model to the actual geometric collision model, the controller 9 selects another stored geometric collision model by which a range of motion of the configuration including the upper back plate 7''' is defined.

In a further alternative embodiment, the surgical table 1 comprises a user interface 12 and the controller 9 is configured to adapt the initial geometric collision model to the actual geometric collision model due to an input to the user interface 12.

Based on a basic configuration merely including the base 2 and the back plate 7", a basic geometric collision model for this basic configuration is stored as the initial geometric collision model. This basic geometric collision model can be adapted to the actual geometric collision model by selecting additional ones of the several components 7, e.g., the leg section 7' and the head plate 7'''', by means of specific buttons on the user interface 12. In alternative embodiments, the selection is performed by another medium or no such selection is provided.

In the further alternative embodiment of the surgical table 1 comprising the user interface 12, the initial geometric collision model can be adapted to the actual geometric collision model by teaching postures of at least one of the several components 7 beyond its respective range of motion defined by the anti-collision algorithm based on the initial geometric collision model. In particular, the input to the user interface 12 is a continuous instruction to move one of the several components 7 beyond its respective range of motion defined by the anti-collision algorithm based on the initial geometric collision model to an intended posture. The controller 9 is configured to apply the intended posture as a limit of a modified range of motion and to adapt the initial geometric collision model to the actual geometric collision model based on the limit of the modified range of motion of the actual configuration. In particular, the controller 9 selects one of already stored geometric collision models which particularly enables reaching of intended posture while maintaining other ranges of motion where possible.

The controller 9 is configured to control a motion of the one of the components 7 beyond the respective range of motion defined by the anti-collision algorithm based on the initial geometric collision model at a velocity reduced with respect to a velocity for moving the respective component 7 within the respective range of motion defined in the anti-collision algorithm based on the initial geometric collision model.

Furthermore, the controller 9 is configured to signal a motion of the one of the components 7 beyond the respective range of motion defined in the anti-collision algorithm based on the initial geometric collision model by an acoustic signal of a beeper.

In alternative embodiments, the velocity for moving beyond the respective range of motion defined by the anti-collision algorithm based on the initial geometric collision model is the same as within this range of motion and/or the motion of the one of the several components 7 beyond the respective range of motion defined in the anti-collision algorithm based on the initial geometric collision model is signaled by means of a visible or another audible signal or it is not signaled.

In a further alternative embodiment, the adaption of the initial geometric collision model to the actual geometric collision model is not performed by the teaching of the posture of the one of the components 7 beyond the respective range of motion but it is only possible by another input to the user interface 12 or by the sensors 10, 11.

The surgical table 1 further comprises a collision sensor 13 configured to detect a collision or an imminent collision between one of several components 7 and another one of the several components 7, the base 2, the supporting surface 6, or an obstacle. The collision sensor 13 is formed by a force sensor which detects a force to one of the several components 7. This sensor 13 is suitable for detecting actual collisions, nevertheless, due to a swift reaction of the controller 9 and the respective one of the drives 8, 8', 8", damage of the surgical table 1 or of an obstacle or injury of a person can be prevented. In alternative embodiments, a collision sensor 13 suitable for preventing an imminent collision, as, e.g., a light barrier, is possible. Furthermore, detecting a course of a motor current is also suitable for detecting a collision.

The controller 9 is configured to adapt the initial geometric collision model such that the anti-collision algorithm defines the respective ranges of motion of the base 2 and/or of the several components 7 such that the collision is prevented. This means that the controller 9 determines a posture of one of the several components 7 right before the collision occurs as a limit for the range of motion defined by the anti-collision algorithm and adapts the initial geometric collision model accordingly to the actual geometric relation model. In particular, the controller 9 selects one of already stored geometric collision models which particularly prevents a motion beyond the posture right before the collision between one of several components 7 and another one of the several components 7, the base 2, the supporting surface 6, or an obstacle while maintaining other ranges of motion occurs where possible.

In use, a method for controlling the surgical table 1 is performed. The method includes the following steps.

Initiating a motion of at least one of the several components 7 and the base 2 to reach a respectively intended posture of the at least one of the several components 7 by the respective drives 8, 8', 8" controlled by the controller 9. The motion is initiated by an input to the user interface 12 or, alternatively, e.g., by speech or gesture control.

Manually checking whether the respective intended posture of the at least one of the several components 7 is reached. It is, for example, visible, that the motion of the at least one of the several components 7 stops and the intended posture of the at least one of the several components 7 is not reached.

If the respective intended posture of the at least one of the components 7 cannot be reached within the ranges of motion defined be the anti-collision algorithm based on the initial geometric collision model, then manually continuously controlling the controller 9 such that the intended posture of the one of the at least one of the components 7 by the respective drives 8, 8', 8" controlled by the controller 9 beyond a limit of the ranges of motion of the components 7 defined by the anti-collision algorithm based on the initial geometric collision model is reached. The continuously controlling of the controller 9 is performed by continuously pressing a button on the user interface 12. Alternatively, another initiation, e.g., by speech or gesture control, is possible.

Adapting the initial geometric collision model according to modified ranges of motion necessary for reaching the intended posture of the one of the components to the actual geometric collision model, wherein the initial geometric collision model is modified by applying the postures of the components necessary for reaching the intended posture of the one of the component as a limit of the ranges of motion. In particular, the controller 9 selects one of already stored geometric collision models which particularly enables reaching of intended posture while maintaining other ranges of motion where possible.

Storing the actual geometric collision model. The actual geometric collision model is stored by the controller 9.

Subsequently defining the respective ranges of motion by the anti-collision algorithm based on the actual geometric collision model and controlling the respective drives 8, 8', 8" to move within the ranges of motion defined based on the actual geometric collision model.

Optionally, the motion of the at least one of the several components 7 and the base 2 beyond the ranges of motion of several components 7 and the base defined by the anti-collision algorithm based on the initial geometric collision model is controlled at a velocity reduced with respect to a velocity for moving the one of the several components 7 and the base 2 within the respective range of motion defined be the anti-collision algorithm based on the initial geometric collision model. By the reduced velocity, in particular, when one of the several components 7 approaches an obstacle or another one of the several components 7, the base 2, or the supporting surface 6, an improved possibility for recognizing a potential risk for a collision is enabled.

Also optionally, the motion of the at least one of the several components 7 and the base 2 beyond the respective range of motion defined by the anti-collision algorithm based on the initial geometric collision model is signaled. The motion is signaled by an acoustic means, e.g., a beeper, or by an optical signal.

The actual geometric collision model is reset to the initial geometric collision model when subsequently waking up the controller 9 from a standby. When bringing the surgical table 1 into a standby situation, for example, after a surgical intervention, the controller 9 resets to the initial geometric collision model since the configuration of the surgical table 1 necessary for a subsequent surgical intervention or other circumstances could have been changed. Therefore, an original safety state is restored. Alternatively, the geometric collision model is not reset to the initial geometric collision model but the actual geometric relation model is maintained.

Again optionally, when detecting the collision or the imminent collision within the range of motion defined based on the active initial or actual geometric collision model, an active initial or actual geometric collision model is adapted such that the collision is prevented.

While the disclosure has been illustrated and described in detail in the drawings and the foregoing description, such illustration and description are to be considered illustrative or exemplary and not restrictive. The disclosure is not limited to the disclosed embodiments. From reading the present disclosure, other modifications will be apparent to a person skilled in the art. Such modifications may involve other features, which are already known in the art and may be used instead of or in addition to features already described herein. In the claims, the word "comprising" does not exclude other elements or steps, and the indefinite article "a" or "an" does not exclude a plurality.

Although this disclosure refers to specific embodiments, it will be understood by those skilled in the art that various changes in form and detail may be made without departing from the subject matter set forth in the accompanying claims.

The invention claimed is:

1. A surgical table comprising:
a base configured to be supported by a supporting surface, the base provided with a base drive configured to move at least a portion of the base relative to the supporting surface;
a plurality of components supportable by the base, one or more of the plurality of components being provided with a respective component drive configured to move the respective component with respect to another one of the plurality of components or to the base;
wherein the base and at least a subset of the plurality of components when supported by the base form a configuration of the surgical table;
and
a controller configured to store, and adapt, a geometric collision model including: object model datasets defining a respective geometry of each of the plurality of components, of the base, and of the supporting surface; and motion compute datasets defining kinematic relationships and ranges of motion of the base, and of the plurality of components,
wherein the controller is configured to store as the geometric collision model a pre-defined initial geometric collision model of a baseline configuration of the surgical table, the baseline configuration defined by the specific plurality of components initially present on the surgical table; detect a modification of the baseline configuration of the surgical table by changing one or more components to thereby modify the object model datasets to an actual configuration of the surgical table after the modification; and to adapt the initial geometric collision model to the actual geometric collision model according to an actual configuration of the surgical table, and store said actual geometric collision model as the geometric collision model,
and
wherein the controller is further configured to execute an anti-collision algorithm, defining respective ranges of motion of the base and each of the subset of the plurality of components supported by the base in dependence on the stored geometric collision model, the anti-collision algorithm being configured to control the base drive to move the at least a portion of the base, and to control the respective component drive to move the respective one of the plurality of components, only within the defined respective ranges of motion such that a collision between any of the subset of the plurality of components, the base, and the supporting surface is prevented.

2. The surgical table of claim 1, wherein a plurality of configurations of the surgical table, each having a different arrangement of the subset of the plurality of components or a different subset of the plurality of components, are pre-defined, and the controller is further configured to store an initial geometric collision model for each of the pre-defined plurality of configurations.

3. The surgical table of claim 2, comprising a sensor configured to detect an attachment of one of the plurality of components to a specific location of the surgical table, and wherein the controller is configured to select one of the plurality of initial geometric collision models as the geometric collision model according to a detection of the attachment of the one of the components to the specific location of the surgical table.

4. The surgical table of claim 1, comprising a user interface, and wherein the controller is configured to adapt the initial geometric collision model to the actual geometric collision model in response to an input to the user interface.

5. The surgical table of claim 4, wherein the input to the user interface is a continuous instruction to move at least one of the subset of the plurality of components, and/or the base, to an intended position beyond its respective range of motion defined by the anti-collision algorithm, and the controller is configured to apply the intended position as a limit of a modified range of motion and to adapt the stored geometrical collision model to the actual geometric collision model based on the limit of the modified range of motion of the actual configuration.

6. The surgical table of claim 5, wherein the controller is configured to control a motion of the at least one of the subset of the plurality of components, and/or the base, beyond its respective range of motion defined by the anti-collision algorithm at a velocity reduced with respect to a velocity for moving the at least one of the subset of the plurality of components within its respective range of motion defined by the anti-collision algorithm.

7. The surgical table of claim 6, wherein the controller is configured to signal a, or the, motion of the at least one of the subset of the plurality of components, and/or the base, beyond its respective range of motion defined in the anti-collision algorithm.

8. The surgical table of claim 7, comprising a sensor configured to detect an attachment of one of the plurality of components to a specific location of the surgical table, and wherein the controller is configured to adapt the stored geometric collision model to the actual geometric collision model based on a detection of the one of the plurality of components attached to the specific location of the surgical table.

9. The surgical table of claim 8, comprising a collision sensor configured to detect a collision, or an imminent collision, between one of the plurality of components and another one of the subset of the plurality of components, the base, the supporting surface, or an obstacle, and wherein the controller is configured to adapt the stored geometric collision model such that the anti-collision algorithm defines the respective ranges of motion of the base and of the subset of the plurality of components such that the collision is prevented.

10. The surgical table of claim 9, wherein the object model datasets comprise bounding boxes, and wherein the anti-collision algorithm calculates whether an intersection point of at least two bounding boxes exists.

11. The surgical table of claim 5, wherein the controller is configured to signal a, or the, motion of the at least one of the subset of the plurality of components, and/or the base, beyond its respective range of motion defined in the anti-collision algorithm.

12. The surgical table of claim 1, comprising a sensor configured to detect an attachment of one of the plurality of components to a specific location of the surgical table, and wherein the controller is configured to adapt the stored geometric collision model to the actual geometric collision model based on a detection of the one of the plurality of components attached to the specific location of the surgical table.

13. The surgical table of claim 1, comprising a collision sensor configured to detect a collision, or an imminent collision, between one of the plurality of components and another one of the subset of the plurality of components, the base, the supporting surface, or an obstacle, and wherein the controller is configured to adapt the stored geometric collision model such that the anti-collision algorithm defines the respective ranges of motion of the base and of the subset of the plurality of components such that the collision is prevented.

14. The surgical table of claim 1, wherein the object model datasets comprise bounding boxes, and wherein the anti-collision algorithm calculates whether an intersection point of at least two bounding boxes exists.

15. A method for controlling a surgical table of claim 1, the method including the steps:
initiating a motion of at least one of the subset of the plurality of components, and/or the at least a portion of the base, to reach an intended position of the at least one of the subset of the plurality of components, and/or the base, by controlling the respective component drive, or base drive by the controller;
manually checking whether the intended position is reached;
if the intended position of the at least one of the subset of the plurality of components, and/or the base, cannot be reached within the ranges of motion defined by the anti-collision algorithm, then manually continuously providing input to the controller, to control the respective component drive, and/or the base drive, such that the intended position of the at least one of the subset of the plurality the components, and/or the base, beyond the ranges of motion defined by the anti-collision algorithm, is reached;
adapting the stored geometric collision model according to modified ranges of motion necessary for reaching the intended position, wherein the stored geometric collision model is adapted by applying the positions of the subset of the plurality of components and the base necessary for reaching the intended position of the at least one of the subset of the plurality of components, and/or the base, as limits of the ranges of motion;
storing the adapted geometric collision model; and
subsequently defining the respective ranges of motion by the anti-collision algorithm based on the stored geometric collision model and controlling the base drive and the respective component drive to move within the ranges of motion defined based on the stored geometric collision model.

16. The method of claim 15, including the step:
controlling a motion of the at least one of the subset of the plurality of components, and/or the base, beyond their respective ranges of motion defined by the anti-collision algorithm at a velocity reduced with respect to a velocity for moving the at least one of the subset of the plurality of components, and/or the base, within the respective range of motion defined by the anti-collision algorithm.

17. The method of claim 15, including the step:
signaling the motion of the at least one of the plurality of components, and/or the base, beyond the respective range of motion defined by the anti-collision algorithm.

18. The method of claim 15, including the step: when detecting a collision, or an imminent collision, within the range of motion defined based on the stored geometric collision model, adapting the stored geometric collision model such that the collision is prevented.

19. A method of operating a surgical table comprising
a base configured to be supported by a supporting surface, the base provided with a base drive configured to move at least a portion of the base relative to the supporting surface;
a plurality of components supportable by the base, one or more of the plurality of components being provided with a respective component drive configured to move the respective component with respect to another one of the plurality of components or to the base;
wherein the base and at least a subset of the plurality of components when supported by the base form a configuration of the surgical table;
and
a controller configured to store, and adapt, a geometric collision model including: object model datasets defining a respective geometry of each of the plurality of components, of the base, and of the supporting surface; and motion compute datasets defining kinematic relationships and ranges of motion of the base, and of the plurality of components,
wherein the controller is configured to store as the geometric collision model a pre-defined initial geometric collision model of a baseline configuration of the surgical table and to adapt the initial geometric collision model to an actual geometric collision model according to an actual configuration of the surgical table, and store said actual geometric collision model as the geometric collision model,
and
wherein the controller is further configured to execute an anti-collision algorithm, defining respective ranges of motion of the base and each of the subset of the plurality of components supported by the base in dependence on the stored geometric collision model, the anti-collision algorithm being configured to control the base drive to move the at least a portion of the base, and to control the respective component drive to move the respective one of the plurality of components, only within the defined respective ranges of motion such that a collision between any of the subset of the plurality of components, the base, and the supporting surface is prevented,
the method comprising the steps of:
initiating a motion of at least one of the subset of the plurality of components, and/or the at least a portion of the base, to reach an intended position of the at least one of the subset of the plurality of components, and/or the base, by controlling the respective component drive, or base drive by the controller;
manually checking whether the intended position is reached;
if the intended position of the at least one of the subset of the plurality of components, and/or the base, cannot be reached within the ranges of motion defined by the anti-collision algorithm, then manually continuously providing input to the controller, to control the respective component drive, and/or the base drive, such that the intended position of the at least one of the subset of the plurality the components, and/or the base, beyond the ranges of motion defined by the anti-collision algorithm, is reached;
adapting the stored geometric collision model according to modified ranges of motion necessary for reaching the intended position, wherein the stored geometric collision model is adapted by applying the positions of the subset of the plurality of components and the base necessary for reaching the intended position of the at least one of the subset of the plurality of components, and/or the base, as limits of the ranges of motion;
storing the adapted geometric collision model;
subsequently defining the respective ranges of motion by the anti-collision algorithm based on the stored geometric collision model and controlling the base drive and the respective component drive to move within the ranges of motion defined based on the stored geometric collision model; and resetting the stored geometric collision model to the initial geometric collision model when subsequently waking up the controller from a standby.

20. A surgical table comprising:

a base configured to be supported by a supporting surface, the base provided with a base drive configured to move at least a portion of the base relative to the supporting surface;

a plurality of components supportable by the base, one or more of the plurality of components being provided with a respective component drive configured to move the respective component with respect to another one of the plurality of components or to the base;

wherein the base and at least a subset of the plurality of components when supported by the base form a configuration of the surgical table;

and a controller configured to store, and adapt, a geometric collision model including: object model datasets defining a respective geometry of each of the plurality of components, of the base, and of the supporting surface; and motion compute datasets defining kinematic relationships and ranges of motion of the base, and of the plurality of components, wherein the controller is configured to store as the geometric collision model a pre-defined initial geometric collision model of a baseline configuration of the surgical table and to adapt the initial geometric collision model to an actual geometric collision model according to an actual configuration of the surgical table, and store said actual geometric collision model as the geometric collision model, and wherein the controller is further configured to execute an anti-collision algorithm, defining respective ranges of motion of the base and each of the subset of the plurality of components supported by the base in dependence on the stored geometric collision model, the anti-collision algorithm being configured to control the base drive to move the at least a portion of the base, and to control the respective component drive to move the respective one of the plurality of components, only within the defined respective ranges of motion such that a collision between any of the subset of the plurality of components, the base, and the supporting surface is prevented, and resetting the stored geometric collision model to the initial geometric collision model when subsequently waking up the controller from a standby.

* * * * *